(12) United States Patent
Faulkner et al.

(10) Patent No.: US 12,011,469 B2
(45) Date of Patent: Jun. 18, 2024

(54) PARENTERAL DELIVERY DEVICE AND METHODS OF USE

(71) Applicant: Vireo Systems, Inc., Madison, TN (US)

(72) Inventors: Mark C. Faulkner, Madison, TN (US); Deeannah Seymour, Franklin, TN (US)

(73) Assignee: Vireo Systems, Inc., Madison, TN (US)

( * ) Notice: Subject to any disclaimer, the term of this patent is extended or adjusted under 35 U.S.C. 154(b) by 0 days.

(21) Appl. No.: 15/987,729

(22) Filed: May 23, 2018

(65) Prior Publication Data

US 2018/0339003 A1 Nov. 29, 2018

Related U.S. Application Data

(60) Provisional application No. 62/509,841, filed on May 23, 2017.

(51) Int. Cl.
| | |
|---|---|
| *A61K 35/747* | (2015.01) |
| *A61K 9/00* | (2006.01) |
| *A61K 9/02* | (2006.01) |
| *A61K 9/48* | (2006.01) |
| *A61K 31/702* | (2006.01) |
| *A61K 33/22* | (2006.01) |
| *A61P 31/10* | (2006.01) |
| *A61K 47/02* | (2006.01) |

(52) U.S. Cl.
CPC .......... *A61K 35/747* (2013.01); *A61K 9/0034* (2013.01); *A61K 9/02* (2013.01); *A61K 9/48* (2013.01); *A61K 9/4825* (2013.01); *A61K 9/485* (2013.01); *A61K 9/4858* (2013.01); *A61K 31/702* (2013.01); *A61K 33/22* (2013.01); *A61P 31/10* (2018.01); *A61K 47/02* (2013.01)

(58) Field of Classification Search
None
See application file for complete search history.

(56) References Cited

U.S. PATENT DOCUMENTS

| 7,708,988 B2 * | 5/2010 | Farmer ................ A61K 31/496 |
| | | 424/93.45 |
| 10,258,567 B1 * | 4/2019 | Krebs-Bensch ........ A61P 15/02 |
| 2005/0053648 A1 * | 3/2005 | Chalmers ............. A61K 9/2072 |
| | | 424/451 |
| 2008/0193428 A1 * | 8/2008 | Zhou .................... A61K 31/192 |
| | | 514/1.1 |

(Continued)

FOREIGN PATENT DOCUMENTS

| CN | 103768095 A | * 5/2014 |
| WO | WO2003/080813 | * 10/2003 |

OTHER PUBLICATIONS

Prutting (Infectious Diseases in Obstetrics and Gynecology 6:191-194 (1998)).*

(Continued)

*Primary Examiner* — Nicole P Babson
(74) *Attorney, Agent, or Firm* — Bradley Arant Boult Cummings LLP

(57) ABSTRACT

A parenteral delivery device and method of delivering a multi-system treatment to a centralized location where the delivery device includes at least an inner compartment encapsulating a first system and an outer compartment encapsulating a second system and the first and second systems have different mechanisms of action for use in the treatment of vaginal infection.

18 Claims, 9 Drawing Sheets

(56) References Cited

U.S. PATENT DOCUMENTS

| | | | | |
|---|---|---|---|---|
| 2013/0101678 A1* | 4/2013 | Gordon | ................ | A61K 31/198 |
| | | | | 424/641 |
| 2016/0143962 A1* | 5/2016 | Berry | ................... | A61K 9/0031 |
| | | | | 424/93.3 |
| 2017/0071990 A1* | 3/2017 | De Seta | ................. | A61K 33/22 |
| 2017/0312228 A1* | 11/2017 | Cade | ................... | A61K 9/4808 |

OTHER PUBLICATIONS

English translation of CN-103768095-A (Year: 2014).*
Ogbolu, David & Oni, Anthony & Daini, Oluwole & Oloko, A.P . . . In Vitro Antimicrobial Properties of Coconut Oil on Candida Species in Ibadan, Nigeria. Journal of medicinal food. 10. 384-7. (Year: 2007).*
Clinical Infection Diseases 1996: 22:726-7.
Cribby S, Taylor M, Reid G., Vaginal Microbiota and the Use of Probiotics: Interdisciplinary Perspectives on Infectious Diseases 2008; 2008:256490.

* cited by examiner

PARENTERAL DELIVERY DEVICE AND METHODS OF USE

FIELD OF THE INVENTION

The present invention relates to a parenteral delivery device and method of delivering a multi-system treatment to a centralized location. In particular, the present invention relates to a delivery device including at least two compartments where an inner compartment encapsulates a first system and an outer compartment encapsulates a second system and the first and second systems have different mechanisms of action for use in the treatment of vaginal candidiasis and similar conditions.

BACKGROUND OF THE INVENTION

A healthy female genital tract is naturally acidic and contains beneficial bacteria that help defend against infections and maintain a normal pH level, i.e., about 3.8 to 4.5. Certain species of *Lactobacillus* genus help maintain an optimal pH and a healthy balance of beneficial microorganisms in the vagina by excluding harmful bacteria and other pathogens present in the female genital tract, such as the small number of yeast cells, under control. In fact, vaginal candidiasis (yeast infection) may be the result of an unbalanced pH that allows too many yeast cells to grow in the female genital tract. Most yeast infections are caused by a type of yeast called *Candida albicans*. However, *Candida glabrata* has also become an increasingly common cause of infection that tends to be more resistant to other treatments.

For a small percentage of affected individuals, vaginal candidiasis is chronic, returning at least 4 times a year (unrelated to antibiotic use). While vaginal candidiasis is common and causes discomfort associated with pruritus, vulvovaginal burning, and dyspareunia, such an infection is generally not serious. However, in some cases, vaginal candidiasis can leave the infected more susceptible to serious issues like fertility problems, infections, sexually transmitted diseases and pelvic inflammatory disease.

The imbalance in pH may be caused by a number of things including antibiotics, corticosteroids, high estrogen levels caused by pregnancy or hormone therapy, low estrogen levels caused by, for example, menopause, uncontrolled diabetes, and HIV infection. Over-the-counter treatments, such as antifungal creams and oral antifungal tablets, can kill the yeast infection and/or harmful bacteria, but do not restore the pH balance. These products use azoles and treatment can span 1 to 7 days. The type of azole varies brand to brand (e.g., miconazole is used in Monistat®; clotrimazole in Gyne-Lotrimin®; butoconazole in Gynazole®). A terconazole cream, which must be prescribed, is typically used to address non-*albicans* strains. For vaginal candidiasis requiring a more aggressive treatment than a cream, the oral antifungal fluconazole may be prescribed.

However, while anti-fungal medications might treat the infection itself, they may also cause harm. In fact, such medications kill off both the good and bad bacteria in the female genital tract, as well as many favorable bacteria in the gut if taken orally. The lack of good bacteria in the female genital tract may contribute to an increased likelihood of urinary tract infections and vaginal candidiasis. Indeed, just like some bacterial infections are resistant to antibiotics, some fungi no longer respond to the antifungal medications that are designed to cure them. There is a growing concern over antifungal resistance for invasive infections with the fungus *Candida*. Some types of *Candida*, e.g., *Candida glabrata*, are becoming resistant to fluconazole. See, e.g., Clinical Infection Diseases 1996: 22:726-7.

In a large percentage of women, a *Lactobacillus* species is dominant in the female genital tract. Thus, it is not surprising that probiotic supplements containing species of *Lactobacillus* have been shown to be helpful in encouraging a balanced vaginal environment. See. e.g., Cribby S, Taylor M, Reid G., Vaginal Microbiota and the Use of Probiotics: Interdisciplinary Perspectives on Infectious Diseases 2008; 2008:256490. However, there is evidence that taking *Lactobacillus* by mouth or eating yogurt enriched with *Lactobacillus* does not prevent vaginal candidiasis after antibiotics. Indeed, probiotics taken orally, may be rendered ineffective even before digestion because heat and stomach acid can kill them. Moreover, probiotics simply die over time. At least one Australian study found no benefit to the use of probiotics, either taken orally or administered via suppository, in the prevention or treatment of vaginal candidiasis when used during antibiotic therapy.

Some affected individuals have also relieved symptoms associated with vaginal candidiasis through the use of tea tree oil. In fact, tea tree oil has been shown in several lab and animal studies to act as an antifungal against yeast. Moreover, tea tree oil contains gamma terpinene and alpha terpinene, which inhibit the growth of the fungus.

In addition, since boric acid is a natural antifungal and antiseptic, and studies have shown that it inhibits the growth of *Candida albicans*, as well as *Candida glabrata*, the use of a boric acid suppository has generally been found to be an effective over-the-counter treatment for vaginal candidiasis.

Bacterial vaginosis (BV), which has similar symptoms as a yeast infection, is also caused by pathogenic bacteria in the female genital tract. BV is typically treated with both oral and intravaginal antibiotics, such as metronidazole and nitroimidazole, with a success rate of about 70 percent to about 80 percent within one month of treatment. However, resistance to antibiotic treatment may occur from *G vaginalis* and other anaerobes, such as *Atopobium* species, that aggregate in vaginal biofilms and prevent the antibiotic from reaching the organism. Moreover, there is a high recurrence rate of BV after antibiotic treatment, e.g., at least 50 percent at one year after treatment, and side effects in about 10 to 20 percent of affected individuals, including secondary vaginal infection with *candida*.

Based on the issues with conventional treatment of vaginal infections, there remains a need for holistic approach to treating vaginal infections such as vaginal candidiasis and BV that inhibits the growth of too much yeast and/or bad bacteria in the female genital tract, but does not negatively impact healthy bacteria therein, and also promotes a healthy vaginal environment to prevent or reduce the risk of future infection.

SUMMARY OF THE INVENTION

The present invention is directed to a delivery device including: a first compartment including a synbiotic, wherein the synbiotic includes about 5 mg to about 150 mg by weight of a dry prebiotic and about 5 to about 500 mg by weight of a dry probiotic; a second compartment including a powder, wherein the powder includes about 60 mg to about 600 mg hydrogen borate, and wherein the second compartment is disposed about the first compartment.

In one embodiment, the prebiotic includes a bifidogenic oligosaccharide selected from the group consisting of fructo-oligosaccharide, galacto-oligosaccharide, inulin, isomalto-oligosaccharide, lactulose, soy-oligosaccharide, xylo-oligosaccharide, and combinations thereof. In another embodiment, the delivery device is in the form of a suppository. In yet another embodiment, the dry prebiotic and the dry probiotic are each in the form of a powder.

In this aspect of the invention, the first compartment may have a first diameter and the second compartment may have a second diameter, wherein the first diameter is between about 55 percent to about 80 percent of the second diameter. In one embodiment, the first compartment has a first length and the second compartment has a second length, and wherein the first length is at between about 15 percent and 40 percent of the second length. In another embodiment, the first compartment and the second compartment are each in the form of a capsule.

The present invention also relates to a vaginal delivery device including: a first capsule having a first dissolution rate and enclosing a powder, wherein the powder includes about 60 mg to about 600 mg hydrogen borate, a second capsule having a second dissolution rate and including a synbiotic powder, wherein the synbiotic powder includes about 5 mg to about 150 mg by weight of a dry prebiotic powder and about 5 mg to about 500 mg by weight of a dry probiotic powder, wherein the first capsule is disposed about the second capsule, and wherein the first dissolution rate is greater than the second dissolution rate. In one embodiment, the first dissolution rate is between about 2 minutes and 15 minutes and the second dissolution rate is between about 30 minutes and about 90 minutes.

In this aspect of the invention, the dry prebiotic powder may include a short chain fructo-oligosaccharide. In another embodiment, the synbiotic further includes a preservative. In still another embodiment, the first capsule has a first length and the second capsule has a second length, and wherein the second length is about 10 percent to about 40 percent less than the first length. The dry probiotic powder may include *Lactobacillus Iners, Lactobacillus crispatus, Lactobacillus gasseri, Lactobacillus jensenii*, or combinations thereof.

The present invention is also directed to a method of treating or preventing vaginal candidiasis including: providing a vaginal suppository including: a first compartment including a synbiotic, wherein the synbiotic includes about 5 mg to about 150 mg by weight of a dry prebiotic and about 5 mg to about 500 mg by weight of a dry probiotic; a second compartment including a powder, wherein the powder includes about 60 mg to about 600 mg hydrogen borate, and wherein the second compartment is disposed about the first compartment; and administering the vaginal suppository to the subject.

In one embodiment, the administering step further includes inserting the vaginal suppository into the vagina of the subject. In another embodiment, the inserting step is repeated once daily for at least three days. In yet another embodiment, the synbiotic includes about 50 mg to about 150 mg of the prebiotic and about 40 mg to about 500 mg of the probiotic. In still another embodiment, the dry probiotic includes *Lactobacillus Iners, Lactobacillus crispatus, Lactobacillus gasseri, Lactobacillus jensenii*, or combinations thereof. In this aspect of the invention, the first compartment may have a first diameter and the second compartment may have a second diameter, wherein the first diameter is between about 55 percent to about 80 percent of the second diameter. In addition, the first compartment may have a first length and the second compartment may have a second length, wherein the first length is at between about 15 percent and 40 percent of the second length.

BRIEF DESCRIPTION OF THE DRAWINGS

Further features and advantages of the invention can be ascertained from the following detailed description that is provided in connection with the drawing(s) described below.

The drawings are not to scale and are intended to depict only typical aspects of the invention, and therefore should not be considered as limiting the scope of the invention. In the drawings, like numbering represents like elements between the drawings.

DETAILED DESCRIPTION OF THE INVENTION

The present invention is directed to a parenteral delivery device including at least two separate systems with different and distinct mechanisms of action for use in the treatment of vaginal infections such as vaginal candidiasis, bacterial vaginosis, and similar conditions. The present invention further contemplates suitable methods to produce and use the parenteral delivery device.

Without being bound by any particular theory, the parenteral delivery device alters the pH of the female genital tract with the first system and locally introduces good bacteria and feeds the good bacteria with the second system. For example, in one embodiment, a multi-compartment delivery device includes a pH modifying material in a first compartment and a synergistic combination of probiotics and prebiotics in a second compartment. The pH modifying material lowers the of the female genital tract to kill the bad fungus and/or bacteria present in the female genital tract due to infection and prepares/stabilizes the biome. The synbiotic provides the stabilized biome an infusion of good bacteria and the fuel to allow the good bacteria to thrive and multiply in the female genital tract.

Delivery Device

The delivery device is constructed such that there are separate compartments to contain each of the systems and deliver the systems at different times. While two compartments are discussed below, it is contemplated that the delivery device of the present invention may have more than two compartments. In addition, it is also contemplated that the delivery device includes a multi-capsule system that delivers the ingredients discussed below, i.e., the pH modifying material, the probiotic, and the prebiotic, in the efficacious amounts discussed below.

Figure 1:
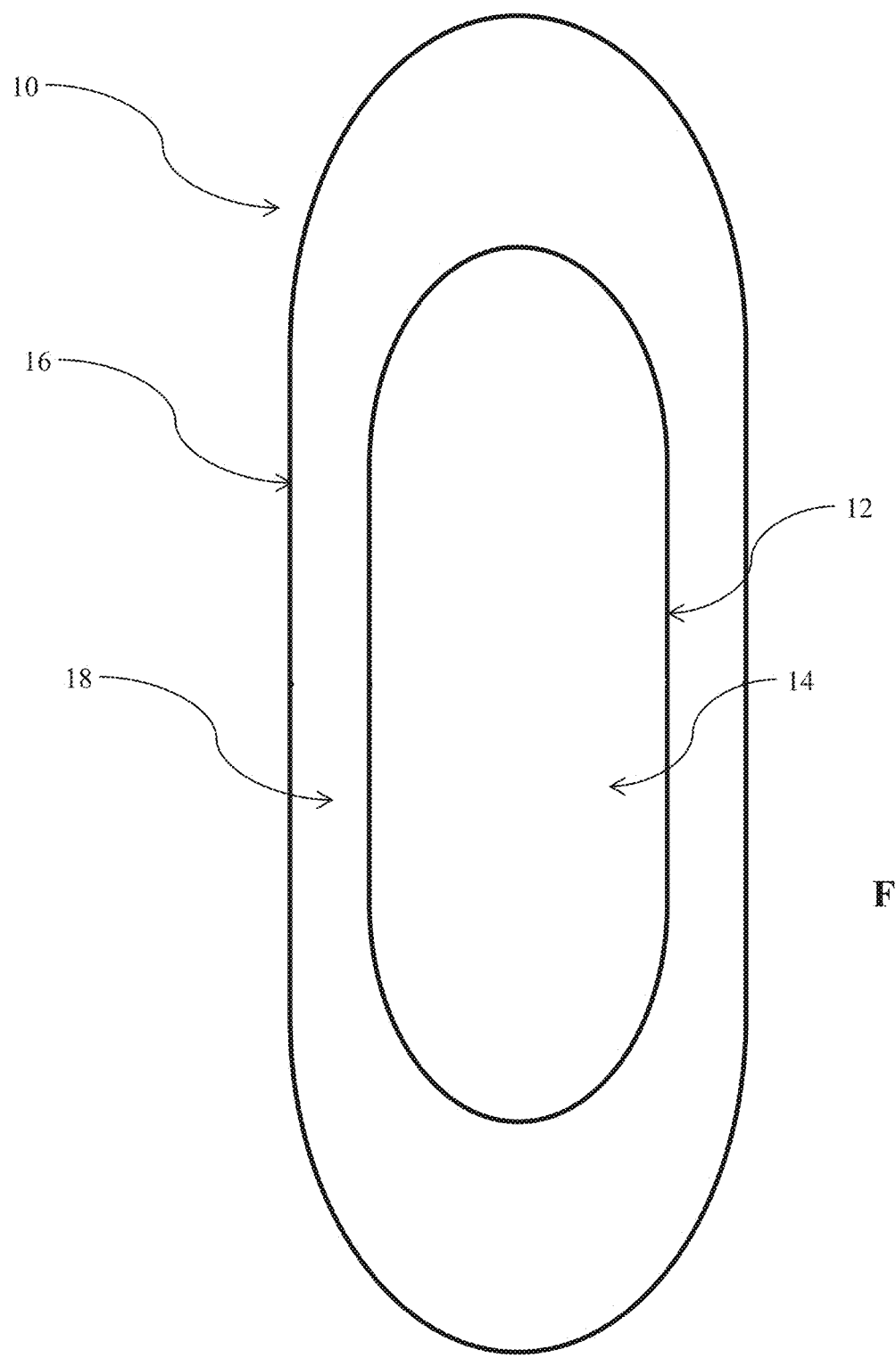
FIG. 1 is a cross-sectional view of a delivery device according to one embodiment of the invention.
Figure 2:
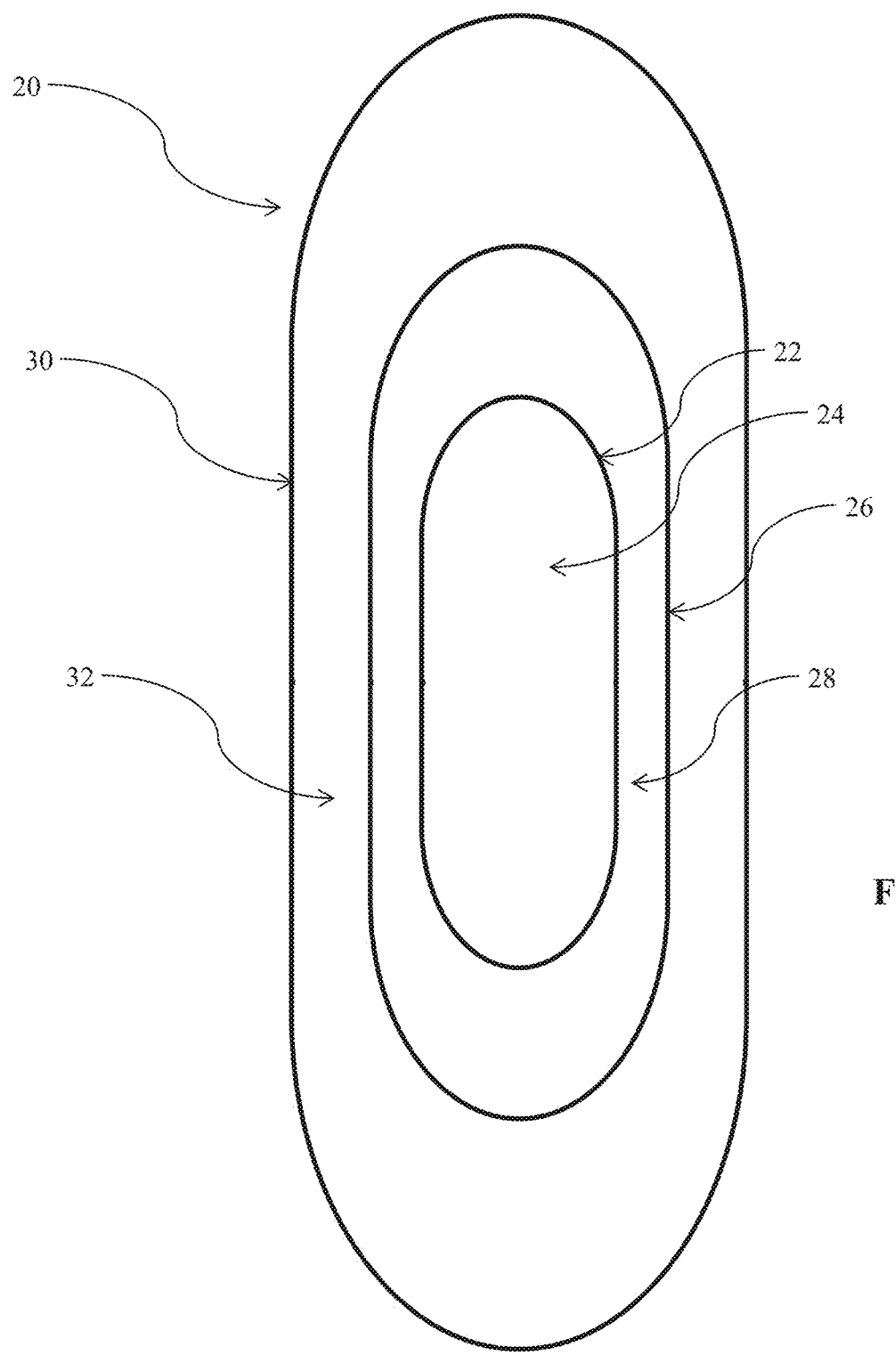
FIG. 2 is a cross-sectional view of a delivery device according to another embodiment of the invention.
Figure 3A:
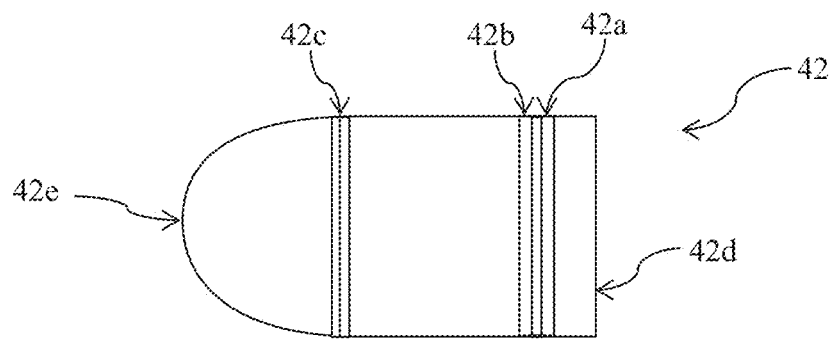
FIGS. 3A-3C is a side-view of separate components of a multi-compartmented container according to one embodiment of the invention.
Figure 3B:
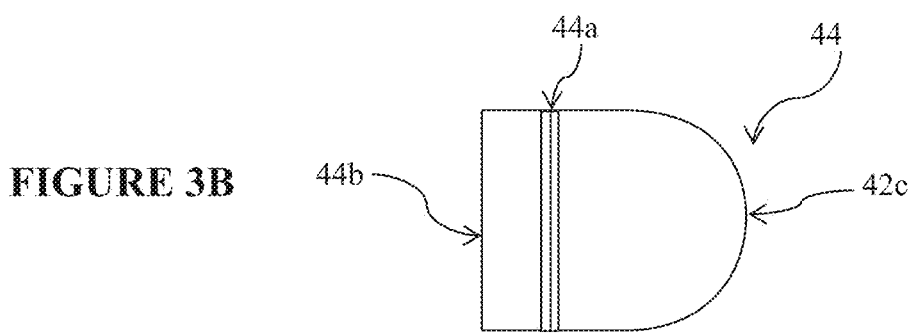
Figure 3C:
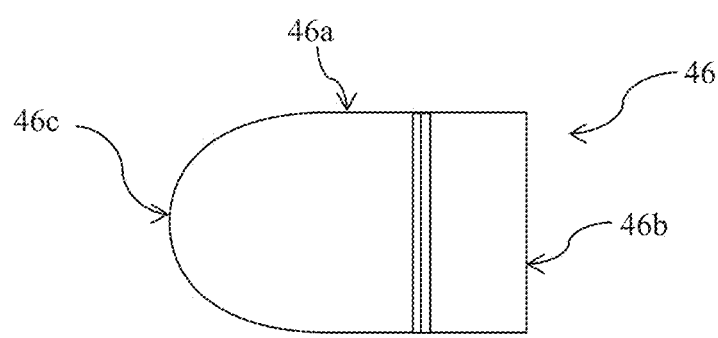
Figure 3D:
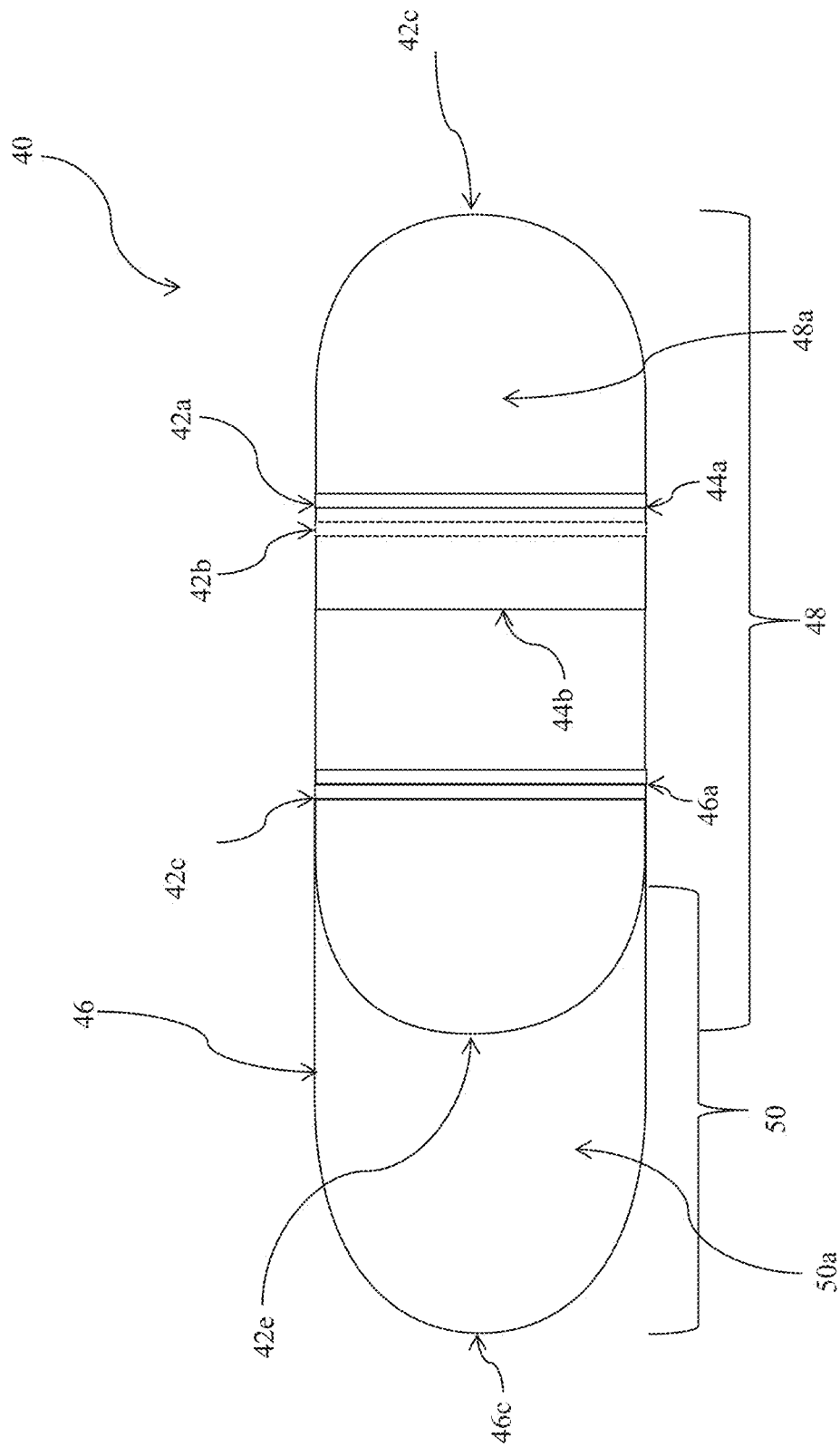
FIG. 3D is a similar view to FIGS. 3A-3C with the components assembled.

In an embodiment shown in FIG. 1, the delivery device 10 includes an inner compartment 12 with contents 14 therein and an outer compartment 16 disposed about the inner compartment 12 with volume therebetween to accommodate the contents 18 of the outer compartment 16. In the embodiment shown in FIG. 2, the delivery device 20 includes an first compartment 22 with contents 24 therein, a second compartment 26 disposed about the first compartment 22 with volume therebetween to accommodate the contents 28 of the second compartment 26, and a third compartment 30 disposed about the second compartment 26 with volume therebetween to accommodate the contents 32 of the third compartment 30.

In one embodiment, the first and second compartments may both be hard capsules each including a cap and a body where the cap has a larger external diameter than the body. In this aspect of the invention, the first (inner) and second (outer) compartments may be made from a number of suitable materials including, but not limited to, hard gelatin (derived from acid-treated raw materials or alkali-treated raw materials), hydroxyl propyl methyl cellulose (HPMC), pullulan, cellulose ethers, such as starches (e.g., waxy maize starch, tapioca dextrin, corn, potato, and derivatives thereof), carrageenan, and polymers or copolymers of (meth)acrylic acids and derivatives thereof.

In one embodiment, the second (outer) compartment is made of a material that allows for dissolution in the female genital tract within about 2 to about 15 minutes. In this aspect, the second (outer) compartment may be made of a material that allows for dissolution in the female genital tract within about 4 minutes to about 12 minutes. In still another embodiment, the second (outer) compartment may be made of a material that allows for dissolution in the female genital tract within about 5 minutes to about 10 minutes.

In another embodiment, the first (inner) compartment is preferably made of a material that allows for delayed release of the contents contained therein such that dissolution of the first (inner) compartment occurs after the second (outer) compartment. In this aspect, the first (inner) compartment may be made of a material that allows for dissolution in the female genital tract within about 30 minutes to about 90 minutes of the dissolution of the second (outer) compartment. For example, the first (inner) compartment may be formed of a material that allows dissolution of the first (inner) compartment within about 40 minutes to about 60 minutes of the dissolution of the second (outer) compartment. In one embodiment, the first (inner) compartment may be made of a material that allows for dissolution in the female genital tract within about 45 minutes to about 55 minutes.

For example, in one embodiment, the first (inner) compartment is a HPMC capsule and the second (outer) compartment is a plant, gelatin, or VCAP low moisture capsule. Suitable examples of plant-based capsules for the second (outer) compartment include, but are not limited to, starch (e.g., from potato, tapioca, or corn) and carrageenan (from seaweed).

In another embodiment, the first (inner) compartment is a HPMC capsule that has a disintegration rate of at least about 45 minutes and the second (outer) compartment is a plant, gelatin, or VCAP low moisture capsule. For example, the first (inner) compartment may have a disintegration rate of about 50 minutes or greater. The first and second compartments may each contain a liquid, a semi-solid formulation (e.g., a slurry), powder, or pellets. For instance, the first and second compartments may each contain a powder.

In yet another embodiment, delayed release of the contents of the first (inner) compartment may be accomplished through osmotic controlled release. For example, the first (inner) compartment may be a rigid tablet and the second (outer) compartment is a plant, gelatin, or VCAP low moisture capsule. In this aspect of the invention, the first and second compartments may each contain a liquid, a semi-solid formulation (e.g., a slurry), powder, or pellets.

In yet another embodiment, the delayed release of the contents of the first (inner) compartment is achieved via microencapsulation, lipid microparticle coating, acrylic coating, chitin coating, gel forming delivery matrices, polymer coatings, ion exchange resin coatings, bio-adhesive mucous bonding coatings, hydrophobic matrices, lipid matrices, hydrophilic matrices, biodegradable matrices, mineral matrices, and combinations thereof. For example, the delayed release of the contents of the first (inner) compartment may be the result of lipid microparticle coating rather than the material used to form the first (inner) compartment. For example, the liquid, semi-solid, powder, or pellets included in the first (inner) compartment may be embedded within lipid multiparticulates (LMPs). The LMPs may be spherical particles having a size ranging from about 50 μm to about 300 μm. The liquid, semi-solid, powder, or pellets may be coated with the LMPs using a fluidized bed process. For example, at least some of the liquid, semi-solid, powder, or pellets included in the first (inner) compartment may be present in an LMP matrix. In addition, amphiphilic excipients may also be used. In one embodiment, solid lipid pellets may be formed by injecting a lipid matrix composed of a hard fat and a glycerol ester into the liquid, semi-solid, powder, or pellets that is intended to be used in the first (inner) compartment. Upon cooling, solid lipid pellets are formed and loaded into the first (inner) compartment.

In yet another embodiment, the first (inner) compartment may be a hard capsule and the outer compartment may be a soft capsule. In this aspect of the invention, the hard capsule that forms the first (inner) compartment may be formed from any of the materials noted above and the second (outer) compartment may be made from soft gelatin, agar, or the like. The hard and soft capsules may each contain a liquid, a semi-solid formulation (e.g., a slurry), powder, or pellets.

Regardless of the type of compartment used for the first (inner) and second (outer) compartments, in this aspect of the invention, the first (inner) compartment is smaller than the second (outer) compartment in terms of empty volume capacity, empty overall closed length, or external diameter so that the second (outer) compartment may be disposed about the inner compartment. In one embodiment, the empty volume capacity (ml) of the first (inner) compartment is between about 20 percent and 60 percent of the empty volume capacity of the second (outer) compartment. For example, the empty volume capacity (ml) of the first (inner) compartment may be between about 25 percent and 60 percent of the empty volume capacity of the second (outer) compartment. In one embodiment, the empty volume capacity (ml) of the first (inner) compartment is between about 30 percent and 40 percent of the empty volume capacity of the second (outer) compartment.

More specifically, in one embodiment, the first (inner) compartment has an empty capsule volume capacity of about 0.27 ml to about 0.78 ml and the second (outer) compartment has an empty volume capacity of about 0.78 ml to about 1.37 ml. In another embodiment, the first (inner) compartment has an empty capsule volume capacity of about 0.36 ml to about 0.78 ml and the second (outer) compartment has an empty volume capacity of about 0.9 ml to about 1.37 ml. In yet another embodiment, the first (inner) compartment has an empty capsule volume capacity of about 0.48 ml to about 0.68 ml and the second (outer) compartment has an empty volume capacity of about 1.00 ml to about 1.37 ml.

The overall closed length of the first (inner) compartment is less than the overall closed length of the second (outer) compartment. In one embodiment, the overall closed length of the first (inner) compartment is about 10 percent to about 40 percent less than the overall closed length of the second (outer) compartment. In another embodiment, the overall closed length of the first (inner) compartment is about 15 percent to about 35 percent less than the overall closed length of the second (outer) compartment. In yet another embodiment, the overall closed length of the first (inner) compartment is about 18 percent to about 25 percent less than the overall closed length of the second (outer) compartment.

The overall closed length of the first (inner) compartment may range from about 0.618 inches to about 0.909 inches. In one embodiment, the first compartment has an overall closed length of about 0.693 inches to about 0.85 inches. In another embodiment, the first (inner) compartment has an overall closed length of about 0.764 inches to about 0.85 inches. The overall closed length of the second (outer) compartment may range from about 0.909 inches to about 1.029 inches. In one embodiment, the second (outer) compartment has an overall closed length of about 0.921 inches to about 1.029 inches. In another embodiment, the second (outer) compartment has an overall closed length of about 0.996 inches to about 1.029 inches.

In this aspect of the invention, the external diameter of the second (outer) compartment is larger than the external diameter of the first (inner) compartment. In one embodiment, the external diameter of the first (inner) compartment is about 55 percent to about 80 percent of the external diameter of the second (outer) compartment. In another embodiment, the external diameter of the first (inner) compartment is about 60 percent to about 78 percent of the external diameter of the second (outer) compartment. In yet another embodiment, the external diameter of the first (inner) compartment is about 70 percent to about 77 percent of the external diameter of the second (outer) compartment.

When both of the first (inner) and second (outer) compartments are hard capsules including a cap and a body, the cap has a larger external diameter than the body. In this aspect of the invention, the first (inner) compartment may include a cap with an empty external diameter that ranges from about 0.230 inches to about 0.301 inches for the cap and a body with an empty external diameter that ranges from about 0.220 inches to about 0.289 inches. In one embodiment, the first (inner) compartment may include a cap with an empty external diameter that ranges from about 0.252 inches to about 0.301 inches for the cap and a body with an empty external diameter that ranges from about 0.240 inches to about 0.289 inches. In another embodiment, the first (inner) compartment may include a cap with an empty external diameter that ranges from about 0.274 inches to about 0.301 inches for the cap and a body with an empty external diameter that ranges from about 0.260 inches to about 0.289 inches. The second (outer) compartment may include a cap with an empty external diameter that ranges from about 0.301 inches to about 0.390 inches for the cap and a body with an empty external diameter that ranges from about 0.289 inches to about 0.375 inches. In one embodiment, the second (outer) compartment may include a cap with an empty external diameter that ranges from about 0.337 inches to about 0.390 inches for the cap and a body with an empty external diameter that ranges from about 0.322 inches to about 0.375 inches. In another embodiment, the first (inner) compartment may include a cap with an empty external diameter that ranges from about 0.338 inches to about 0.375 inches for the cap and a body with an empty external diameter that ranges from about 0.324 inches to about 0.375 inches.

The first (inner) compartment may range from a size 3 capsule to a size 0E capsule. The second (outer) compartment may range from a size 0E capsule to a size 000 capsule. For example, in one embodiment, the first (inner) compartment is a size 0 capsule and the second (outer) compartment is a size 000 capsule. In another embodiment, the first (inner) compartment is a size 3 capsule and the second (outer) compartment is a size 0E capsule. In yet another embodiment, the first (inner) compartment is a size 2 capsule and the second (outer) compartment is a size 00 capsule. In still another embodiment, the first (inner) compartment is a size 1 capsule and the second (outer) compartment is a size 00E capsule. In yet another embodiment, the first (inner) compartment is a size 0E capsule and the second (outer) compartment is a size 000 capsule.

In another embodiment, the delivery device is a multi-compartmented container where each compartment is distinct and separate, but not necessarily constructed such that is has an outer compartment fully disposed about and enclosing the inner compartment. Rather, in this aspect of the invention, the delivery device is a multi-compartmented container including a body, a first cap, and a second cap where the body and the top cap form a first compartment and the bottom cap attaches to a closed end of the first compartment to form the second compartment. For example, as shown in FIGS. 3A-D, the container includes a body 42, a first cap 44, and a second cap 46 such that two distinctly separate compartments are formed and are able to contain different contents. When assembled, the body 40 and the first cap 42 constitute a first compartment 48. When the second cap 46 is fitted onto the closed end 42e of the first compartment 48, a second compartment 50 is formed. The components 42, 44, and 46 are designed so that the first cap 44 and the second cap 46 can be telescopically fitted onto the body 42, i.e., the first and second caps can be coaxially and slideably mounted on the outer surface of the body 42.

The body 42 includes a pair of annular grooves 42a, 42b near its open end 42d so that a corresponding inwardly-projecting annular ridge 44a of first cap 44 may alternately engage when open end 44b of first cap 44 is slideably mounted on the outer surface of the body 42. In a first position, annular ridge 44a engages first annular groove 42a, forming a pre-fill position that allows first cap 44 to be removed from the body 42 for filling. Once filled with first contents 48a, first cap 44 and body 42 are placed in a lock position, wherein annular ridge 44a engages annular groove 42b. The disengagement axial force of first cap 44 from body 42 in the pre-fill position is less than the disengagement force of first cap from body 42 in the lock position. Once in the lock position, the body 42 and the first cap 44 may be sealed with a sealing fluid, heat, or some other mechanism.

A second compartment 50 is formed when the open end 46b of second cap 46 is slideably mounted on the closed end 42e of body 42. The body 42 includes a third annular groove 42c near its closed end 42e that may be engaged by an inwardly-projecting annular ridge 46a of second cap 46. In the alternative, the body 42 may include a pair of annular grooves near its closed end 42e so that the second compartment may be formed with pre-fill and lock positions similar to the first compartment. The second compartment may be filled with second contents 50a.

In one embodiment, body 42, first cap 44, and second cap 46 are formed of the same materials. In another embodiment, body 42 and first cap 44 are formed of the same material having a first dissolution or disintegration rate and second cap 46 is formed of a different material having a second dissolution or disintegration rate that is slower than the first dissolution or disintegration rate. As a result, the contents 50a contained in the second compartment 50 will be released after the first contents 48a in the first compartment 48. Without being bound by any particular theory, such a delivery device is beneficial because the first contents 48a kill the bad bacteria present in the biome and stabilize the biome prior to introduction of the second contents 50a.

In yet another embodiment, body 42 and first cap 44 are formed of the same material having a first dissolution or disintegration rate and second cap 46 is formed of a different material having a second dissolution or disintegration rate that is greater than the first dissolution or disintegration rate. As a result, the contents 50a contained in the second compartment 50 will be released before the first contents 48a in the first compartment 48. Without being bound by any particular theory, such a delivery device is beneficial because the contents 50a kill the bad bacteria present in the biome and stabilize the biome prior to introduction of the first contents 48a. U.S. Pat. Nos. 8,968,717 and 9,456,990, incorporated in their entirety by reference herein, disclose other embodiments of a multi-compartmented container suitable for use with the present invention.

In this aspect of the invention, the first compartment, i.e., the body 42 and first cap 44, may have a wide range of dimensions. For illustrative purposes only, the length of the first compartment may range from about 0.3 inches to about 1.0 inch. In one embodiment, the length of the first compartment ranges from about 0.4 inches to about 0.9 inches. In another embodiment, the length of the first compartment ranges from about 0.5 inches to about 0.8 inches. Once the second cap 46 is assembled onto the first compartment, the multi-compartmented container 40 may have a length that ranges from about 0.75 inches to about 1.1 inches. In another embodiment, the multi-compartmented container 40 may have a length that ranges from about 0.8 inches to about 1.0 inch. In yet another embodiment, the length of the multi-compartmented container 40 ranges from about 0.85 inches to about 0.95 inches.

The diameter of the multi-compartmented container 40 ranges from about 0.2 inches to about 0.4 inches. In one embodiment, the container 40 has a diameter that ranges from about 0.22 inches to about 0.38 inches. In another embodiment, the container 40 has a diameter that ranges from about 0.24 inches to about 0.38 inches.

pH Modifying Material

The disclosed delivery device includes a pH modifying material in at least one of the compartments, for example, the second (outer) compartment. The term, "pH modifying material," refers to any material capable of altering the pH of the female genital tract, for example, lowering the pH of the female genital tract. The pH modifying material may also be effective for killing off harmful bacteria and fungus present in the female genital tract. In one embodiment, the pH modifying material may have a pH that ranges from about 8 to 10 in pure water at 25° C. and 1 atm. In another embodiment, the pH modifying material may include lactic acid, ascorbic acid, hydrogen borate (also referred to as boric acid), or combinations thereof. In still another embodiment, the pH modifying material is hydrogen borate.

The pH modifying material may be formulated as a solid. For example, the pH modifying material may be formulated as a powder, pellet, or granule. In another embodiment, the pH modifying material may be formulated as a liquid or a semi-solid formulation. For instance, the pH modifying material may be formulated as a slurry or an emulsion.

In one embodiment, the pH modifying material is formulated as a powder. For instance, the pH modifying material may include hydrogen borate in powder form. In this aspect, the pH modifying material may be used in an amount of about 50 mg to about 600 mg. In another embodiment, the pH modifying material may be used in an amount of about 60 mg to about 600 mg. In another embodiment, the pH modifying material may be used in an amount of about 100 mg to about 550 mg. In still another embodiment, the pH modifying material may be used in an amount of about 200 mg to about 500 mg. In yet another embodiment, the pH modifying material may be used in an amount of about 250 mg to about 400 mg. In another embodiment, the pH modifying material may be used in an amount of about 275 mg to about 325 mg. For example, the pH modifying material may be used in an amount of about 300 mg.

In another embodiment, the pH modifying material is formulated in a pH modifying slurry. In this aspect, the pH modifying slurry includes the at least one pH modifying material in an oil medium with antifungal properties. The oil medium may be tea tree oil, coconut oil, oregano oil, grape seed oil, lemon oil, peppermint oil, cinnamon oil, or the like, or combinations thereof. In another embodiment, the oil medium is a tea tree oil prepared as a terpinen-4-ol type. In fact, the minimization of 1,8-cineole content in the tea tree oil is preferable to minimize adverse reactions. In yet another embodiment, the oil medium is a coconut oil. In still another embodiment, the oil medium is a blend of tea tree oil and coconut oil. In yet another embodiment, the oil medium is a blend of at least three of the following: tea tree oil, coconut oil, oregano oil, grape seed oil, lemon oil, peppermint oil, and cinnamon oil.

The oil medium may be included in the pH modifying slurry in an amount ranging from about 150 mg to about 1200 mg. In one embodiment, the pH modifying slurry may include about 180 mg to about 1100 mg of oil medium in the pH modifying slurry. In another embodiment, the oil medium may be included in the pH modifying slurry in an amount of about 720 mg to about 850 mg. In another embodiment, the pH modifying slurry may include about 740 mg to about 825 mg of oil medium in the pH modifying slurry. For example, when the outer capsule is a size 00 capsule, the pH modifying slurry may include about 750 mg to about 780 mg of oil medium in the pH modifying slurry.

In another embodiment, the pH modifying slurry may include about 950 mg to about 1200 mg of oil medium in the pH modifying slurry. In yet another embodiment, the oil medium may be included in the pH modifying slurry in an amount of about 1000 mg to about 1150 mg. In still another embodiment, the pH modifying slurry may include about 1020 mg to about 1120 mg of oil medium in the pH modifying slurry. For example, when the outer capsule is a size 000 capsule, the pH modifying slurry includes about 1050 mg to about 1100 mg of oil medium in the pH modifying slurry.

In still another embodiment, the pH modifying slurry may include about 150 mg to about 580 mg of oil medium in the pH modifying slurry. In yet another embodiment, the pH modifying slurry may include about 180 mg to about 550 mg of oil medium in the pH modifying slurry. For example, when the outer capsule is a size 00 capsule, the pH modifying slurry may include about 450 mg to about 480 mg of oil medium in the pH modifying slurry.

In another embodiment, the pH modifying slurry may include about 450 mg to about 900 mg of oil medium in the pH modifying slurry. In yet another embodiment, the oil medium may be included in the pH modifying slurry in an amount of about 500 mg to about 850 mg. For example, when the outer capsule is a size 000 capsule, the pH modifying slurry may include about 750 mg to about 800 mg of oil medium in the pH modifying slurry.

The oil medium may include up to about 45 percent solid materials. In one embodiment, the oil medium includes up to about 30 percent solid materials. In another embodiment, the oil medium includes up to about 20 percent solid materials. In yet another embodiment, the oil medium includes up to about 10 percent solid materials. In still another embodiment, the oil medium includes less than 1 percent solid materials. For example, the oil medium may include less than 0.05 percent solid materials.

The pH modifying slurry may include about 50 mg to about 600 mg of the pH modifying material. In one embodiment, the pH modifying slurry includes about 60 mg to about 550 mg of the pH modifying material. In another embodiment, the pH modifying slurry includes about 200 mg to about 500 mg of the pH modifying material. In still another embodiment, the pH modifying slurry includes about 250 mg to about 400 mg of the pH modifying material. In another embodiment, the pH modifying slurry includes about 275 mg to about 325 mg of pH modifying material. For example, the pH modifying material may be included in the pH modifying slurry in an amount of about 300 mg.

In one embodiment, the pH modifying slurry may include about 18 percent to about 55 percent of the pH modifying material by weight of the pH modifying slurry. In another embodiment, the pH modifying slurry may include about 23 percent to about 53 percent of the pH modifying material by weight of the modifying slurry. In another embodiment, the pH modifying slurry may include about 25 percent to about 45 percent of the pH modifying material by weight of the pH modifying slurry. In still another embodiment, the pH modifying slurry may include about 27 percent to about 40 percent of the pH modifying material by weight of the pH modifying slurry. In yet another embodiment, the pH modifying material is included in an amount of about 30 percent to about 38 percent by weight of the pH modifying slurry. For example, in one embodiment, the pH modifying slurry includes about 38 percent to about 40 percent of the pH modifying material by weight of the pH modifying slurry. In another embodiment, the pH modifying slurry may include about 27 percent to about 29 percent of the pH modifying material by weight of the pH modifying slurry.

In addition, the pH modifying slurry may contain slippery elm powder, garlic powder, calendula, olive leaf extract, gentian violet, grapefruit seed extract, witch hazel, palmarosa oil, onion powder, neem, harad herb, thuja, lavender, chamomile, and combinations thereof.

Moreover, in addition to the pH modifying material, the oil medium, and any of the other ingredients listed above, the pH modifying slurry may contain suitable excipients and auxiliaries that facilitate processing of the slurry. Nonlimiting examples of suitable excipients include tillers such as calcium phosphates (e.g., tricalcium phosphate or calcium hydrogen phosphate) and binders such as starch, paste, using, for example, maize starch, wheat starch, rice starch, potato starch, gelatin, gum tragacanth, vegetable cellulose such as methyl cellulose, ethyl cellulose, hydroxypropyl cellulose, hydroxypropylmethyl cellulose sodium carboxymethylcellulose, and hydroxyethyl methyl cellulose, and/or polyvinyl pyrrolidone.

Symbiotic

As briefly discussed above, the synbiotic is a blend of at least one probiotic and at least one prebiotic. The probiotic and prebiotic may be formulated as a solid. For example, the probiotic and prebiotic may be formulated as a powder, pellet, or granule. In one embodiment, the probiotic and the prebiotic are formulated as powders.

In one embodiment, the synbiotic includes about 5 mg to about 600 mg of probiotics and about 5 mg to about 200 mg of prebiotics. In another embodiment, the synbiotic includes about 5 mg to about 500 mg of probiotics and about 5 mg to about 150 mg of prebiotics. In still another embodiment, the synbiotic includes about 25 mg to about 500 mg of probiotics and about 25 mg to about 150 mg of prebiotics. In another embodiment, the synbiotic includes about 40 mg to about 500 mg of probiotics and about 50 mg to about 150 mg of prebiotics. In still another embodiment, the synbiotic includes about 100 mg, to about 450 mg of probiotics and about 75 mg to about 125 mg of prebiotics. In yet another embodiment, the synbiotic includes about 400 mg of probiotics and 100 mg of prebiotics.

Suitable probiotics for use in the synbiotic are any number of defined viable microorganisms that reach the female genital tract in an active state and thus exert positive health effects. In one embodiment, a species of *Lactobacillus* is employed as the probiotic portion of the synbiotic blend. For example, *Lactobacillus iners, Lactobacillus crispatus, Lactobacillus gasseri, Lactobacillus jensenii, Lactobacillus rhamnosus* GG, *Lactobacillus reuteri* (RC-14), *Lactobacillus acidophilus, Lactobacillus delbrueckii, Lactobacillus helveticus, Lactobacillus salivarius, Lactobacillus casei, Lactobacillus paracasei, Lactobacillus curvatus, Lactobacillus plantarum, Lactobacillus sakei, Lactobacillus brevis, Lactobacillus buchneri, Lactobacillus fermentum, Bifidobacterium lactis, B. longum,* and combinations thereof are suitable for use as the probiotic in the synbiotic. In another embodiment, the probiotic includes at least one of *Lactobacillus iners, Lactobacillus crispatus, Lactobacillus gasseri, Lactobacillus jensenii,* or combinations thereof. In still another embodiment, the probiotic includes at least one of *Lactobacillus acidophilus* LA02, *Lactobacillus buchneri* Lb26, *Lactobacillus fermentum* ME-3, *Lactobacillus salivarius* subsp. *salivarius* CRL 1328, *Lactobacillus crispatus* CRL 1266, *Lactobacillus paracasei* subsp. *paracasei* CRL 1289, *Lactobacillus gasseri* CRL 1259, *Lactobacillus plantarum* LP02, *Lactobacillus delbrueckii* subsp. *bulgaricus* LDB-1, and combinations thereof. Without being bound by any particular theory, it is believed that the inhibition of growth and virulence of the fungal pathogen *Candida albicans* via the hydrogen peroxide produced by *Lactobacillus* species that occurs in the gut will also occur in the female genital tract.

In another embodiment, the probiotic employed includes *Bifidobacterium* and certain strains of *Lactobacillus casei* or the *Lactobacillus acidophilus*-group. In yet another embodiment, the probiotic employed includes any of the above species of *Lactobacillus* and *Escherichia coli* strain Nissle 1917, *Enterococcus faecium* SF68, the probiotic yeast *Saccharomyces boulardii*, or combinations thereof.

Prebiotics differ from probiotics in that they act as a fertilizer for the good bacteria that is already present in the body. In addition, whereas probiotics are live bacteria that are susceptible to heat, acid, and time, prebiotics are indigestible dietary fibers that are not destroyed in the body because they are not susceptible to heat, cold, acid, or time. Suitable prebiotics for use in the synbiotic are any number of selectively fermented ingredients that allows specific changes, both in the composition and/or activity in the female genital tract. Examples include, but are not limited to, bifidogenic oligosaccharides such as fructo-oligosaccharide, inulin, lactulose, galactooligosaccharide, isomalto-oligosaccharide, soy-oligosaccharide, and xylo-oligosaccharide. In one embodiment, the prebiotic includes short chain fructo-oligosaccharides (scFOS). The scFOS may be derived from beet or sugar cane.

In one embodiment, the synbiotic includes about 25 mg to about 200 mg of scFOS and about 25 mg to about 600 mg of *Lactobacilli*. In another embodiment, the synbiotic includes about 50 mg to about 175 mg of scFOS and about 40 mg to about 500 mg of *Lactobacilli*. In still another embodiment, the symbiotic includes about 80 mg to about 140 mg of scFOS and about 75 mg to about 400 mg of *Lactobacilli*.

In one embodiment, the synbiotic includes an excipient such as rice flour. In another embodiment, the synbiotic includes a flow agent such as silicon dioxide or microcrystalline cellulose to aid the powder in flowing into the capsules during the filling process.

The synbiotic may also be suspended in a base. In one embodiment, the base may be polyethylene glycol, hydrogenated vegetable oils, cocoa butter, *Theobroma* oil, hydrogenated corn oil, palm oil, palm kernel oil, coconut oil, or combinations thereof. When a base is present, it may be used in an amount of about 50 percent to about 90 percent by weight of the synbiotic.

The synbiotic may also include a preservative, a suspending agent (when a base is used), or both. Suitable preservatives include, but are not limited to, methylparaben, propylparaben, potassium sorbate, benzalkonium chloride, benzethonium chloride, and combinations thereof. When used, the preservative may be present in an amount of about 0.1 percent to about 0.2 percent by weight of the synbiotic. Suitable suspending agents include, but are not limited to, silicon dioxide, bentonite, hydrated aluminum silicate, and mixtures thereof. When used, the suspending agent may be present in an amount of about 0.1 percent to about 2.0 percent by weight.

Methods of Making

Starting materials useful for preparing compounds and intermediates thereof, and/or practicing methods described herein are commercially available or can be prepared by well-known synthetic methods. For example, when the pH modifying material is hydrogen borate, the hydrogen borate may be prepared by reacting borax (sodium tetraborate decahydrate) with a mineral acid, such as hydrochloric acid:

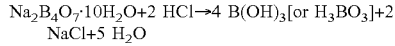

It may also be formed as a by-product of hydrolysis of boron trihalides and diborane:

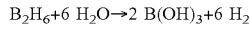

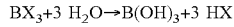

where X may be Cl, Br, I.

As discussed above, in one embodiment, the crystalline pH modifying material may be mixed with an oil medium or base to create the pH modifying slurry. In one embodiment, about 4 to about 15 percent of the pH modifying material based on total volume of the pH modifying slurry is added to the oil medium. In another embodiment, about 5 to about 12 percent of the pH modifying material based on total volume of the pH modifying slurry is added to the oil medium. In yet another embodiment, about 8 to about 10 percent of the pH modifying material based on total volume of the pH modifying slurry is added to the oil medium. The oil medium is present in the pH modifying slurry in an amount of about 85 percent to about 96 percent based on the total volume of the pH modifying slurry. In one embodiment, the oil medium is present in the pH modifying slurry in an amount of about 88 percent to about 95 percent based on the total volume of the pH modifying slurry. In another embodiment, about 90 percent to about 92 percent of the oil medium is present in the pH modifying slurry based on the total volume of the pH modifying slurry.

Each compartment of the delivery device may be filled using standard capsule-filling technology, such as intermittent or continuous motion capsule filling machines equipped with dosators. In one aspect of the invention, once the inner compartment is inserted into the body of the outer compartment, the outer compartment is filled and then the cap of the outer compartment is secured to form the delivery device of the present invention. In another aspect of the invention, once the first compartment is filled and securely closed, the second compartment is filled and securely attached to the first compartment.

Methods of Use

The delivery device can be used, for example, to treat or prevent vaginal infections such as vaginal candidiasis, bacterial vaginosis, and similar conditions.

The terms "treat," "treating," and "treatment" as used herein refer to alleviating, reducing, or inhibiting one or more symptoms or physiological aspects of a disease, disorder, syndrome, or condition. "Treatment" as used herein covers any treatment of a disease in a subject, and includes: (a) preventing the disease or symptom from occurring in a subject which may be predisposed to the disease or symptom, but has not yet been diagnosed as having it; (b) inhibiting the disease or symptom, i.e., arresting or preventing its development; (c) reducing the severity of the disease or symptom; or (d) relieving the disease symptom, i.e., causing regression of the disease or symptom.

The terms "prevent," "prevention," and "preventing" refers to administering a composition to a subject at risk for or having a predisposition for one or more symptoms caused by a disease or disorder to cause cessation of a particular symptom of the disease or disorder, a reduction or prevention of one or more symptoms of the disease or disorder, a reduction in the severity of the disease or disorder, the complete ablation of the disease or disorder, or stabilization or delay of the development or progression of the disease or disorder.

The delivery device can be formulated for administration by parenteral or transmucosal routes of administration. In this aspect, the delivery device may be formulated as a vaginal suppository.

In one embodiment, the present disclosure provides for a method of treatment and/or prevention of a vaginal infection, such as vaginal candidiasis, bacterial vaginosis, and similar conditions, in a subject in need thereof, the method including administering the delivery device to the subject. The term "subject" as used herein refers to a mammal, including, but not limited to, humans, rodents, such as mice and rats, and other laboratory animals. The delivery device may be administered to the subject by inserting the delivery device into the vagina of the subject. If, after the administration of the delivery device, the subject is still infected with vaginal candidiasis and/or bacterial vaginosis, then an optional step of the method is to continue administration of the delivery device.

An effective treatment may range from about 3-7 delivery devices over a 7-day period. In one embodiment, two delivery devices are inserted in the female genital tract (optionally at bedtime) for seven continuous days. For example, when the delivery device includes about 200 mg to about 400 mg of the pH modifying material, two delivery devices per day may be used. In another embodiment, one delivery device is inserted in the female genital tract (optionally at bedtime) for seven continuous days. For example, when the delivery device includes more than about 400 mg and up to about 600 mg of the pH modifying material, one delivery device per day may be used. For recurring yeast infections, the treatment above is used for two weeks, and then the delivery device may be used twice a week for six months to one year.

Once the outer (or first) compartment has dissolved and the contents have been delivered to the female genital tract, the inner (or second) compartment starts to dissolve and the contents are delivered to the female genital tract. The multi-compartment delivery device allows for the different systems to be separated until such times as they are released.

The disclosed delivery device can be administered to a subject in need thereof in combination or alternation with other therapies and therapeutic agents. In some embodiments, the disclosed delivery device and the additional therapeutic agent are administered separately, but simultaneously, or in alternation. The additional therapeutic agent can also be administered as part of the disclosed delivery device.

EXAMPLES

The following non-limiting examples are merely illustrative of the preferred embodiments of the present invention, and are not to be construed as limiting the invention, the scope of which is defined by the appended claims.

Example 1

A delivery device with a size 0 inner capsule and a size 000 outer capsule. The inner capsule is a HPMC capsule filled with a powder blend of 100 mg powdered scFOS and 150 mg of *Lactobacillus Iners*, 125 mg of *Lactobacillus crispatus*, 75 mg *Lactobacillus gasseri*, and 50 mg of *Lactobacillus jensenii*. The inner capsule is placed inside the body of the outer capsule and then filled with 600 mg of pH modifying slurry before securing the cap of the outer capsule. The pH modifying slurry includes 300 mg of hydrogen borate and 300 mg of tea tree oil. The outer capsule is a gelatin capsule.

Example 2

Hydrogen Borate Demonstrates Anti-Yeast Activity

Materials and Methods
*Candida albicans*, ATTC number 10231, was used as a test organism. Cultures of *C. albicans* were grown in a rotator overnight at room temperature in tubes of LB-broth. The cultures contained approximately $1 \times 10^8$ organisms per mL. The suspension was diluted 1:1000 in LB-broth and 50 microliters were spread on the surface of a LB-agar plate, i.e., approximately 5,000 organisms.

A well was punched into the agar following the application of *C. albicans* and 60 mg of the hydrogen borate (boric acid) was added to the well followed by 25 microliters of water. Plates were incubated at 37 degrees centigrade overnight and observed for growth and/or a zone of inhibition (clear area) around the well containing the hydrogen borate.

Figure 4:
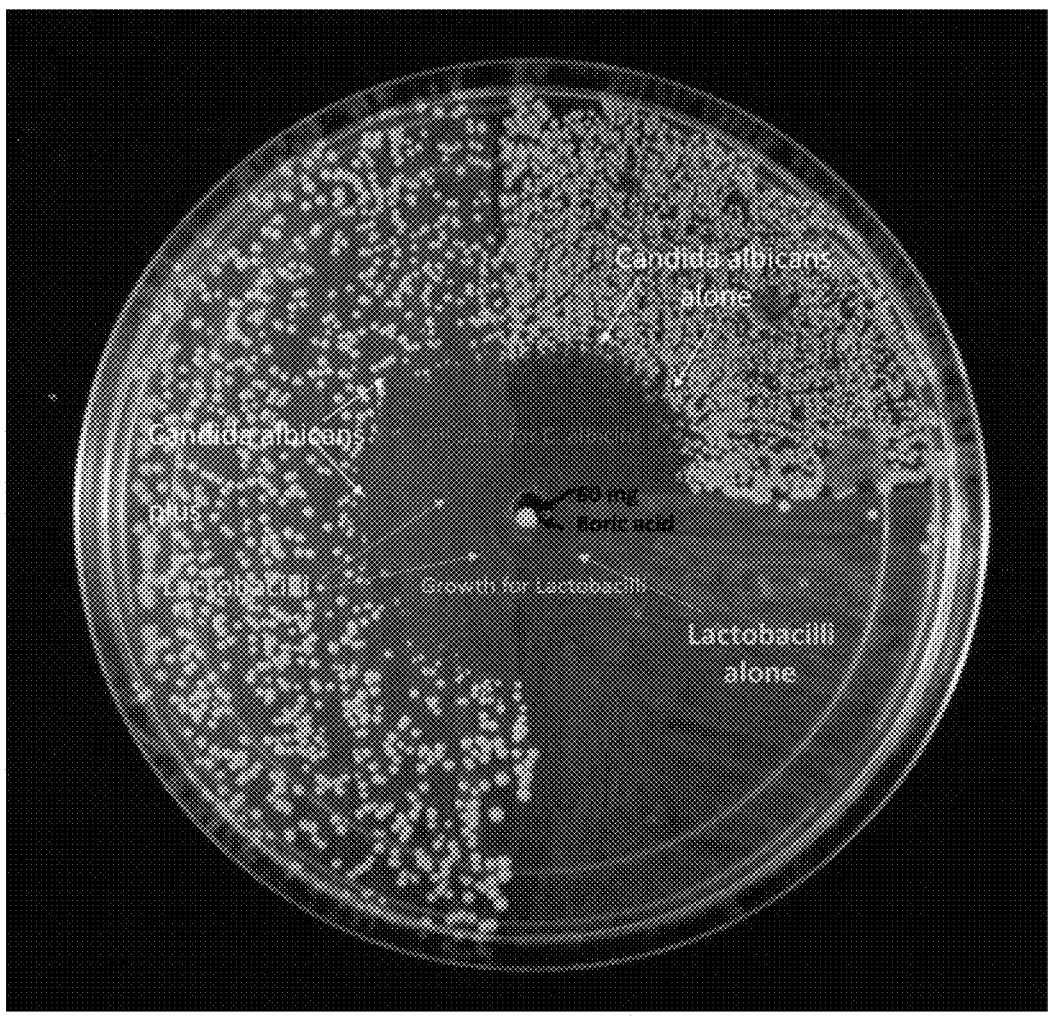
FIGS. 4-6 are photographs of wells showing that hydrogen borate demonstrates anti-*Candida albicans* activity.
Figure 5:
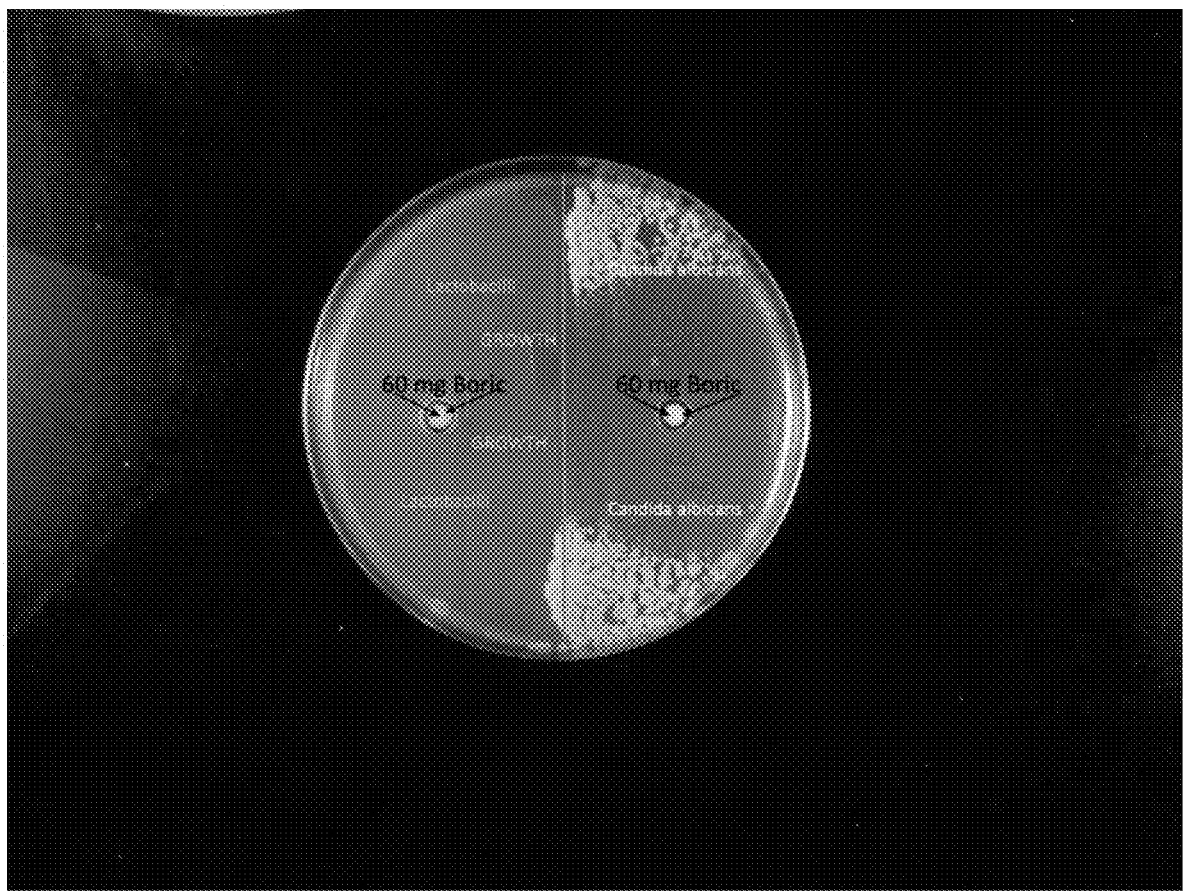
Figure 6:
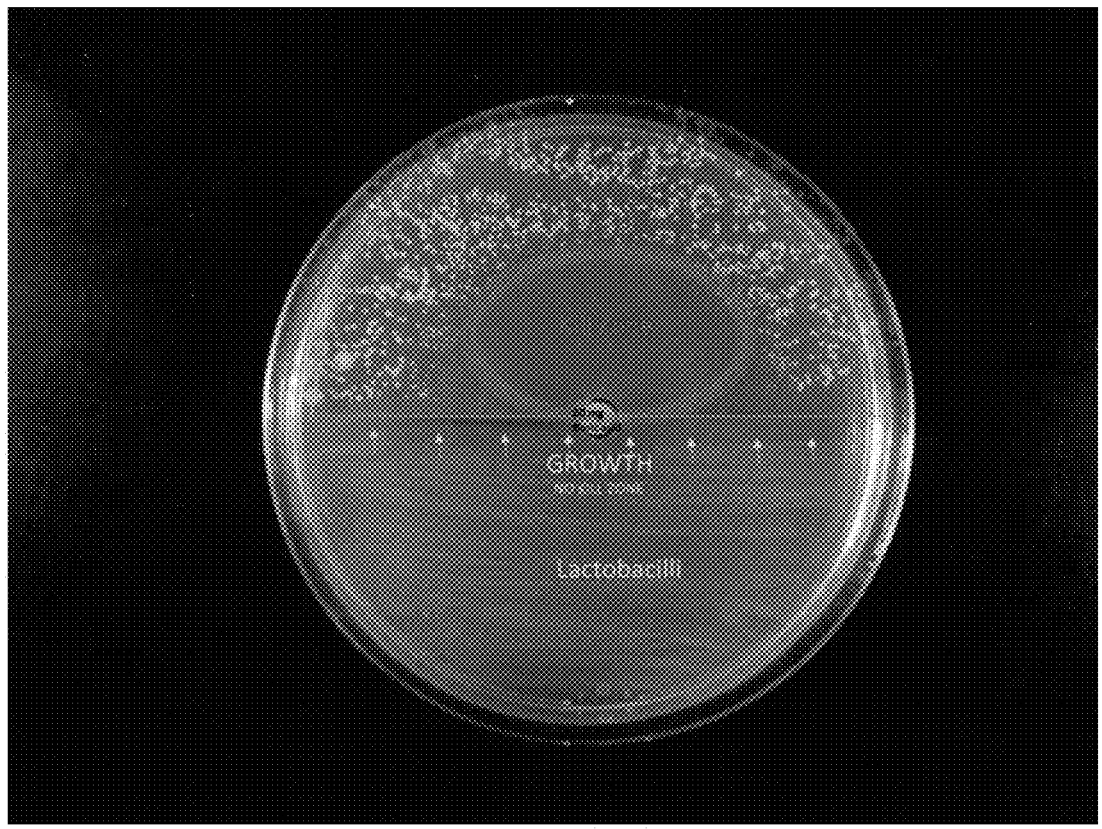

Results
As shown in FIGS. 4-6, the hydrogen borate demonstrated anti-*Candida albicans* activity. FIGS. 4-6 show that the hydrogen borate (60 mg) generated a zone of inhibition (represented by the clear area) against the yeast, *Candida albicans*. In particular, as shown, the hydrogen borate generated a 45 mm zone of inhibition against the yeast, *Candida albicans*.

Example 3

Hydrogen Borate does not Affect the Growth of *Lactobacilli*

Materials and Methods
*Lactobacillus* capsular material (40 mg) was suspended in 1.0 milliliter of LB-broth and 25 microliters was spread on the surface of half of an LB-agar plate. For comparison, the other half of the plate spread with *C. albicans*. A hole was punched in the middle of the plate and 60 mg of hydrogen borate was added. The plates were incubated overnight and scored for growth and/or a zone of inhibition around the hydrogen borate well.

In some cases, only about a quarter of the LB-agar plate was spread with the L-capsular suspension in which case only 10 microliters was used.

In some cases, the *C. albicans* was co-cultured with the *Lactobacilli*. For this inoculum, equal volumes of the two suspensions of organisms described earlier were mixed and used to spread on LB-agar plates for testing for any effect of the co-culture on the anti-yeast activity of hydrogen borate or any effect on *Lactobacillus* growth.

Figure 7:
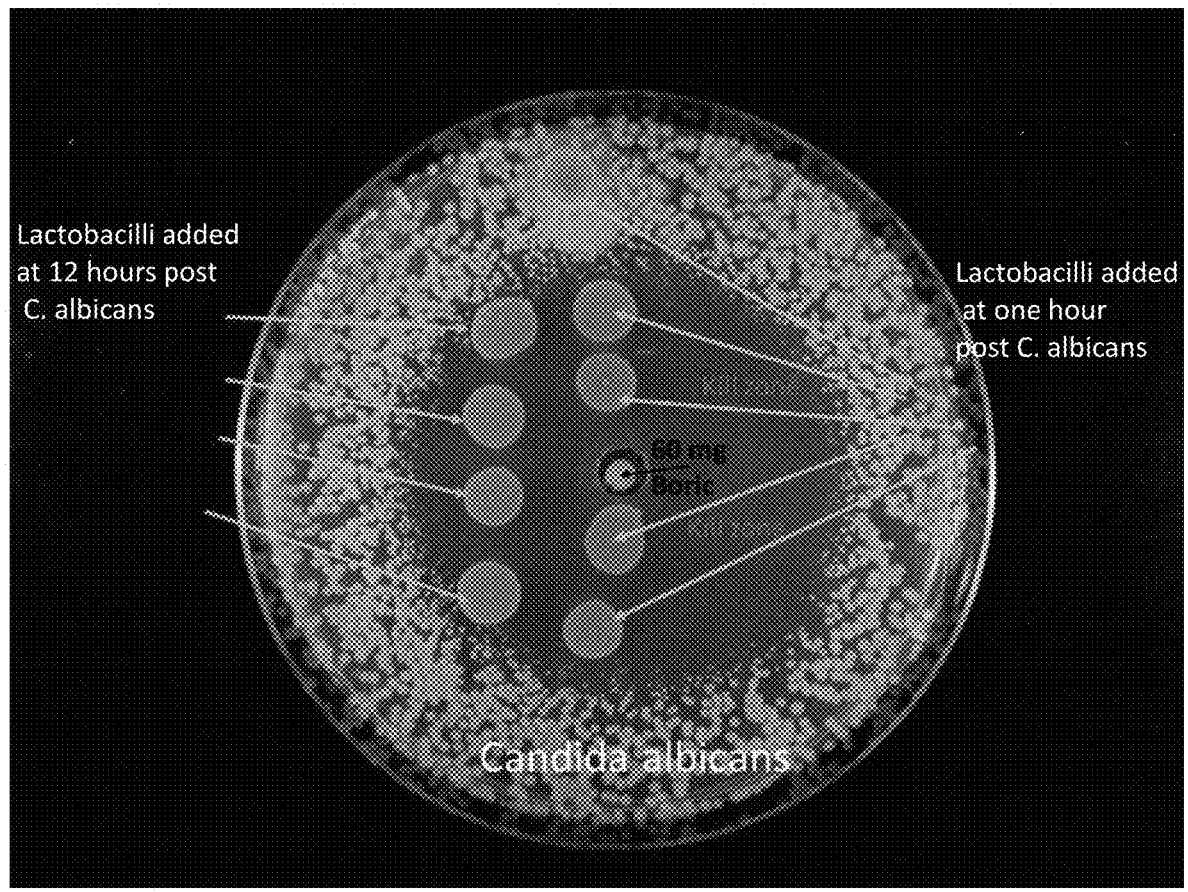
FIG. 7 is a photograph of a well showing that hydrogen borate does not have an effect on the growth of *Lactobacilli*.

Results
As shown in FIG. 7, the hydrogen borate did not have an effect on the growth of *Lactobacilli*. Regardless of whether the *Lactobacilli* was added to the kill zones one hour or 12 hours after the hydrogen borate was put in the wells, there was no demonstrable effect on the growth of the *Lactobacilli*.

Figure 8:
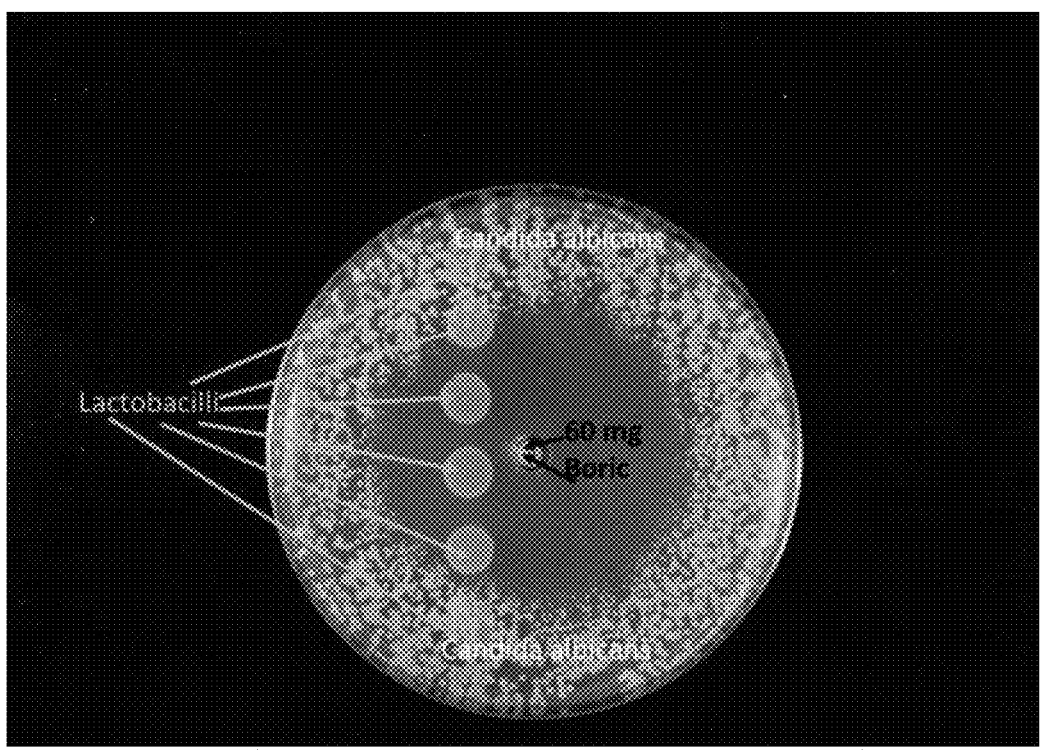
FIG. 8 is a photograph of a well showing that co-cultures of *C. albicans* and *Lactobacilli* do not affect the activity of hydrogen borate.

FIG. 8 shows a co-culture of *C. albicans* and *Lactobacilli* where *Lactobacilli* was added dropwise immediately after *C. albicans* was spread onto the plate. As shown in FIG. 8, co-cultures of *C. albicans* and *Lactobacilli* did not affect the activity of the hydrogen borate. When the *C. albicans* and *Lactobacilli* were tested separately, the positive anti-yeast activity remained active and there was a lack of activity against *Lactobacilli*. The co-culture experiment also showed that the growth of the two organisms do not appear to affect each other.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. For example, it is also contemplated that effective treatment may occur using a delivery mechanism that includes a multi-capsule delivery system where one capsule contains the pH modifying slurry and another contains the synbiotic blend in the amounts described above. In addition, it is contemplated that effective treatment may be accomplished with a multi-capsule delivery system including one capsule including the pH modifying slurry, one capsule containing the probiotic, and one capsule containing the prebiotic in the amounts described above. When such a multi-capsule delivery system is used, the capsule containing the pH modifying slurry may be inserted at the same time as the capsule containing the synbiotic or, if separate, capsules containing the probiotic and prebiotic. In the alternative, the capsule containing the pH modifying slurry may be first inserted and then, after predetermined period of time, the capsule containing the synbiotic or, if separate, capsules containing the probiotic and prebiotic may be inserted. In one embodiment, the predetermined period of time before the insertion of the capsule containing the synbiotic or, if separate, capsules containing the probiotic and prebiotic is between about 30 minutes and 2 hours, preferably about 45 minutes to about 75 minutes, and more preferably about 55 minutes to about 65 minutes. Such modifications are also intended to fall within the scope of the appended claims. All patents and patent applications cited in the foregoing text are expressly incorporate herein by reference in their entirety.

What is claimed is:

1. A delivery device, comprising:
    a first compartment comprising a synbiotic, wherein the synbiotic comprises about 75 mg to about 125 mg by weight of a dry prebiotic and about 100 mg to about 450 mg by weight of a dry probiotic, wherein the dry probiotic comprises *Lactobacillus Iners, Lactobacillus crispatus, Lactobacillus gasseri, Lactobacillus jensenii*, or combinations thereof;
    a second compartment comprising a slurry, wherein the slurry consists of about 50 mg to about 600 mg hydrogen borate and about 150 mg to about 580 mg of an oil medium, and wherein the second compartment is disposed about the first compartment.

2. The delivery device of claim 1, wherein the prebiotic comprises a bifidogenic oligosaccharide selected from the group consisting of fructo-oligosaccharide, galacto-oligosaccharide, inulin, isomalto-oligosaccharide, lactulose, soy-oligosaccharide, xylo-oligosaccharide, and combinations thereof.

3. The delivery device of claim 1, wherein the device is in the form of a suppository.

4. The delivery device of claim 1, wherein the dry prebiotic and the dry probiotic are each in the form of a powder.

5. The delivery device of claim 1, wherein the first compartment has a first diameter and the second compartment has a second diameter, and wherein the first diameter is between about 55 percent to about 80 percent of the second diameter.

6. The delivery device of claim 1, wherein the first compartment has a first length and the second compartment has a second length, and wherein the first length is at between about 15 percent and 40 percent of the second length.

7. The delivery device of claim 1, wherein the first compartment and the second compartment are each in the form of a capsule.

8. The vaginal delivery device of claim 1, wherein the oil medium is coconut oil.

9. The vaginal delivery device of claim 1, wherein the hydrogen borate is present in the slurry in an amount of about 250 mg to about 400 mg.

10. A vaginal delivery device comprising:
    a first capsule having a first dissolution rate and enclosing a slurry, wherein the slurry consists of about 200 mg to about 500 mg hydrogen borate and about 150 mg to about 580 mg coconut oil,
    a second capsule having a second dissolution rate and comprising a synbiotic powder, wherein the synbiotic powder comprises about 75 mg to about 125 mg by weight of a dry prebiotic powder and about 100 mg to about 450 mg by weight of a dry probiotic powder, wherein the dry probiotic powder comprises *Lactobacillus Iners, Lactobacillus crispatus, Lactobacillus gasseri, Lactobacillus jensenii*, or combinations thereof,
    wherein the first capsule is disposed about the second capsule, and
    wherein the first dissolution rate is greater than the second dissolution rate.

11. The vaginal delivery device of claim 10, wherein the first dissolution rate is between about 2 minutes and 15 minutes and the second dissolution rate is between about 30 minutes and about 90 minutes.

12. The vaginal delivery device of claim 10, wherein the dry prebiotic powder comprises a short chain fructo-oligosaccharide.

13. The vaginal delivery device of claim 10, wherein the synbiotic powder further comprises a preservative.

14. The vaginal delivery device of claim 10, wherein the first capsule has a first length and the second capsule has a second length, and wherein the second length is about 10 percent to about 40 percent less than the first length.

15. A vaginal delivery device comprising:
    a first capsule enclosing a slurry, wherein the slurry consists of hydrogen borate and an oil medium, wherein the oil medium is present in the slurry in an amount of about 150 mg to about 580 mg,
    a second capsule comprising a synbiotic, wherein the synbiotic comprises about 80 mg to about 140 mg by weight of a dry prebiotic powder and about 75 mg to about 400 mg by weight of a dry probiotic powder, wherein the dry prebiotic powder comprises a short chain fructo-oligosaccharide, and wherein the dry probiotic powder comprises *Lactobacillus Iners, Lactobacillus crispatus, Lactobacillus gasseri*, and *Lactobacillus jensenii*, and
    wherein the first capsule is disposed about the second capsule.

16. The vaginal delivery device of claim 15, wherein the oil medium is coconut oil.

17. The vaginal delivery device of claim 15, wherein the first capsule has a first dissolution rate and the second capsule has a second dissolution rate, wherein the first dissolution rate is greater than the second dissolution rate.

18. The vaginal delivery device of claim 15, wherein the synbiotic further comprises a preservative.

* * * * *